(12) United States Patent
Allan

(10) Patent No.: US 6,540,401 B2
(45) Date of Patent: Apr. 1, 2003

(54) SIDE SEAL CONSTRUCTION FOR A STERILE POUCH

(75) Inventor: Roger J. Allan, Lafayette Hill, PA (US)

(73) Assignee: Mangar Industries, Inc., New Britain, PA (US)

( * ) Notice: Subject to any disclaimer, the term of this patent is extended or adjusted under 35 U.S.C. 154(b) by 0 days.

(21) Appl. No.: 09/851,557

(22) Filed: May 10, 2001

(65) Prior Publication Data

US 2002/0108877 A1 Aug. 15, 2002

Related U.S. Application Data

(60) Provisional application No. 60/268,705, filed on Feb. 15, 2001.

(51) Int. Cl.$^7$ .......................... B65D 30/00; A61B 19/02
(52) U.S. Cl. .......................... 383/107; 206/439; 206/484
(58) Field of Search ................... 206/438, 439, 206/484; 383/107, 200, 210

(56) References Cited

U.S. PATENT DOCUMENTS

| | | | | |
|---|---|---|---|---|
| 2,230,849 A | * | 2/1941 | Salfisberg | 206/484 |
| 2,329,360 A | * | 9/1943 | Salfisberg | 206/484 |
| 3,534,901 A | | 10/1970 | Repko et al. | |
| 3,773,248 A | | 11/1973 | Cecil et al. | |
| 4,097,236 A | * | 6/1978 | Daly et al. | 206/439 |
| 4,630,729 A | * | 12/1986 | Hirt et al. | 206/438 |
| 4,730,726 A | | 3/1988 | Holzwarth | |
| 4,838,429 A | | 6/1989 | Fabisiewicz et al. | |
| 5,131,760 A | * | 7/1992 | Farmer | 383/210 |
| 5,222,600 A | | 6/1993 | Stoddard et al. | |
| 5,418,022 A | | 5/1995 | Anderson et al. | |
| 5,431,622 A | | 7/1995 | Pyrozyk et al. | |
| 5,674,010 A | | 10/1997 | Dussich | |
| 5,727,684 A | | 3/1998 | Webb et al. | |
| 5,746,311 A | | 5/1998 | Brown et al. | |
| 5,830,547 A | | 11/1998 | MacKenzie et al. | |
| 5,839,648 A | | 11/1998 | Brigand et al. | |
| 5,868,244 A | | 2/1999 | Ivanov et al. | |
| 5,971,613 A | * | 10/1999 | Bell | 383/107 |
| 6,009,691 A | | 1/2000 | Lifshey | |
| 6,021,625 A | | 2/2000 | Cerwin et al. | |
| 6,098,800 A | | 8/2000 | Bennish, Jr. et al. | |
| 6,244,747 B1 | * | 6/2001 | Caudle | 383/200 |
| 6,325,542 B1 | * | 12/2001 | Komatsu | 383/210 |

* cited by examiner

Primary Examiner—Bryon P. Gehman
(74) Attorney, Agent, or Firm—Gregory J. Gore

(57) ABSTRACT

A pouch for sterilized materials is formed from two webs positioned face-to-face attached around portions of their edges by heat fusion, thereby forming a pouch having an interior cavity and a mouth being an unsealed portion of the webs along a top edge. An interior boundary line along the inside of the seal area has a wavy configuration which includes a series of inward-facing peaks and valleys. Thus, when the cross-seal is applied to close the pouch, the overlap of the seal areas along the interior boundary is along a wavy line and therefore microbial contamination is inhibited by this tortuous path. A similar tortuous path for preventing microbial contamination is provided in the type of the pouch having a breather panel by cutting a wavy configuration into the side edge of the breather panel web before it is spliced and fused to the other pouch webs.

6 Claims, 3 Drawing Sheets

SIDE SEAL CONSTRUCTION FOR A STERILE POUCH

The present application is related to provisional patent application Ser. No. 60/268,705 entitled "Side Seal Construction for a Sterilizable Pouch" filed on Feb. 15, 2001, priority from which is hereby claimed.

FIELD OF THE INVENTION

The present invention relates generally to pouch packaging of sterile items, such as surgical instruments, to protect them against contamination by microorganisms. More specifically, it relates to the construction of a side-edge closure seal for a sterile pouch.

BACKGROUND OF THE INVENTION

Packaging for medical instruments such as tear-open bags and peelable pouches that are hermetically sealed are well-known. Pouches are delivered to the packager where items are introduced to the pouches and then sealed closed by a final heat-seal process. The final heat-seal applies heat, dwell and pressure to the thermoplastic material of the pouch, fusing both webs of the pouch material together across the pouch opening. In a specific type of pouch, one side of the pouch includes a semipermeable panel which permits the gas sterilization of the contents after sealing. In both instances, there is concern about the integrity of the seal around the perimeter of the bag sidewall. Of greatest concern are the areas of the seal which are transition points between the heat-seal footprint of the manufacturing seal and the closure seal later applied by the packager.

The occurrence of overlapping heat seals is a consequence of separate sealing operations occurring at different times and places. A first sealing operation occurs during the manufacturing of the pouch in which all side edges are sealed except a length of one edge left unsealed to create an opening for the introduction of the packaged items. The second sealing operation is similar to the first but carried out at the packaging site where the opening in the pouch is sealed closed. In order that the seal be continuous throughout the entire perimeter of the pouch, it is necessary for the two seal footprints (surface area where the opposing pouch sidewalls are fused together) to overlap.

In this pouch construction, the overlap joint is the point of least integrity along the length of the seal due to handling of the pouch at times between the two sealing operations. This occurs due to the type of packaging material used which is easily deformable and has no shape memory. The line along which the first and second seal footprints overlap is at the sides of the bag opening and this area is also the point of highest mechanical stress of the bag material as it is handled making it vulnerable to distortion. Thus an imperfect seal may result along the overlap points of the heat-seal footprints of the two above-described sealing operations because of distortions in the material.

In another type of well-known pouch, there is a problem with seal integrity in the areas of transition between thicknesses of a multi-ply construction having a transverse sidewall seam, for example those having a semipermeable panel to provide preliminary gas sterilization prior to final closure. In this construction, a problem can occur along a transverse edge of an intermediate ply of material fused between two outer plies where the edge of the intermediate ply forms the transition line from a three-ply thickness to a two-ply thickness in final construction. Because of the way in which the pouch is manufactured, this transverse internal edge extends to the outside side edge of the pouch and therefore can possibly create a migration channel for microbes entering the pouch from the outside. Furthermore, in this type of bag the perimeter sealing along the edge of the panel is imperfect because the transition in the overall thickness between the different number of layers causes uneven pressure to be applied during the sealing process and therefore imperfections in the perimeter seal can occur.

SUMMARY OF THE INVENTION

The present invention has been devised in order to satisfy the need in the art described above for greater seal integrity of pouch-type containers for sterilized materials to prevent microbial contamination. The applicant has created a pouch-type container comprising two webs positioned face-to-face having peripheral portions of their bottom and side edges joined by heat fusion thereby forming a pouch having an interior cavity. A mouth of the pouch is created by an unsealed portion of the webs along the top edge. The area of fusion creates a peripheral seal footprint along the bottom and side edges. An interior boundary line lies along the inside of the seal footprint facing the interior cavity and it terminates at two points at the sides of the mouth of the pouch. The two end portions of the boundary line proximate the mouth are provided with a wavy configuration which includes a series of inward facing peaks and valleys. This configuration of the heat seal footprint is created by a heat seal die which has a corresponding wavy edge that creates the peaks and valleys along the above-described portion of the heat seal footprint. The geometry of the peaks and valleys can be radiused or jagged, and when the transverse heat seal closure is applied after materials are inserted into the pouch, the closure seal footprint extends across the top edge and overlaps the wavy end portions of the interior boundary line.

To provide greater seal integrity in a sterilizable pouch having a breather panel, a pouch-type container has been created which comprises two opposing faces composed of heat-fusable sheet materials fused in an area along their side and bottom edges. One of the two opposing faces consists of two webs spliced together along a transverse seam which extends the entire width of the face and overlaps a transverse edge of one of said webs being a breather panel material. The transverse edge of the breather panel web is provided with a wavy configuration including a series of peaks and valleys along its entire length. Preferably the breather panel web is composed of a semipermeable material such as Dupont Tyvek®. Because the above-described problem migration channel occurs along the edge of the breather panel, the resulting shape of the channel is a tortuous path for any migrating microbes and hence contamination is prevented.

It is therefore the main object of the present invention to create enhanced seal performance in web-fused sterile pouches to more reliably prevent contamination from outside of the pouch. This object has been achieved by the above-disclosed invention, a preferred embodiment of which is described in detail in the following drawings and description of preferred embodiments.

DESCRIPTION OF THE PREFERRED EMBODIMENT

Figure 1:
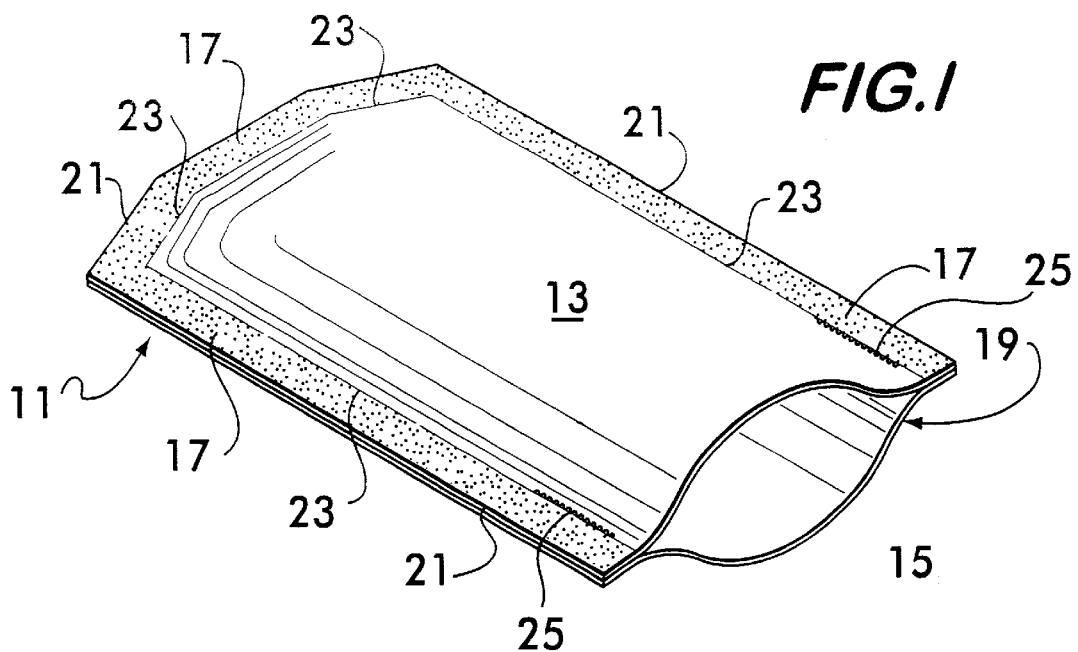
FIG. 1 is a top front left perspective view of the present invention.
Figure 3:
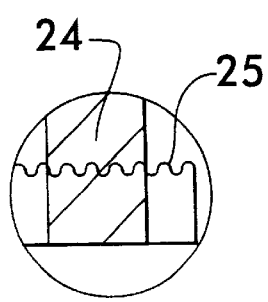
FIG. 3 is an enlarged fragmentary view of the invention as shown in FIG. 2.

Referring now to FIGS. 1 and 3, according to the present invention, a pouch 11 for containing medical instruments after sterilization is disclosed comprising two facing webs 13 and 15 sealed together around their perimeter along side and bottom edges. The pouch is formed by a sealing die which through heat and pressure fuses the side edges and bottom edge of the two webs together creating a seal surface area formed by the footprint 17 of the sealing die. This forms a pouch having an opening along the unsealed top edge 19 to receive the packaged items. On either side of the seal area footprint two boundary lines are formed where the webs meet; an external boundary line 21 and an interior boundary line 23. The interior boundary line defines points along which the webs are fused together facing the interior area of the pouch. This interior boundary line extends around the inside perimeter of the seal footprint to the mouth 19 of the pouch. A short length of the interior boundary line adjacent to the mouth of the pouch opening includes a tooth-shaped portion 25 with peaks and valleys directed inwardly toward the center of the pouch. The peaks and valleys are radiused or jagged to provide a generally wavy shape to this portion of the boundary line near their ends at the mouth of the pouch. The wavy shape of the boundary line edge of the seal footprint is created by a sealing die (not shown) which has a series of inter-projecting teeth that correspond to the resulting wavy shape of the interior boundary line. The pouches thus formed are then handled in any suitable manner and elements to be contained in the pouch are inserted.

Figure 2:
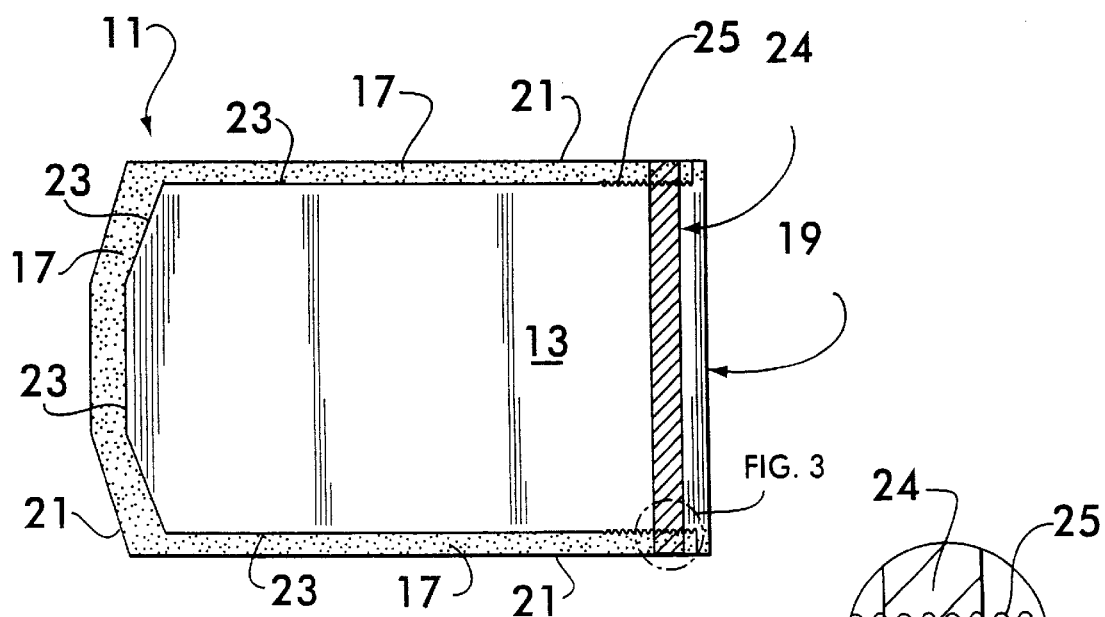
FIG. 2 is a top plan view of the present invention.
Figure 4:
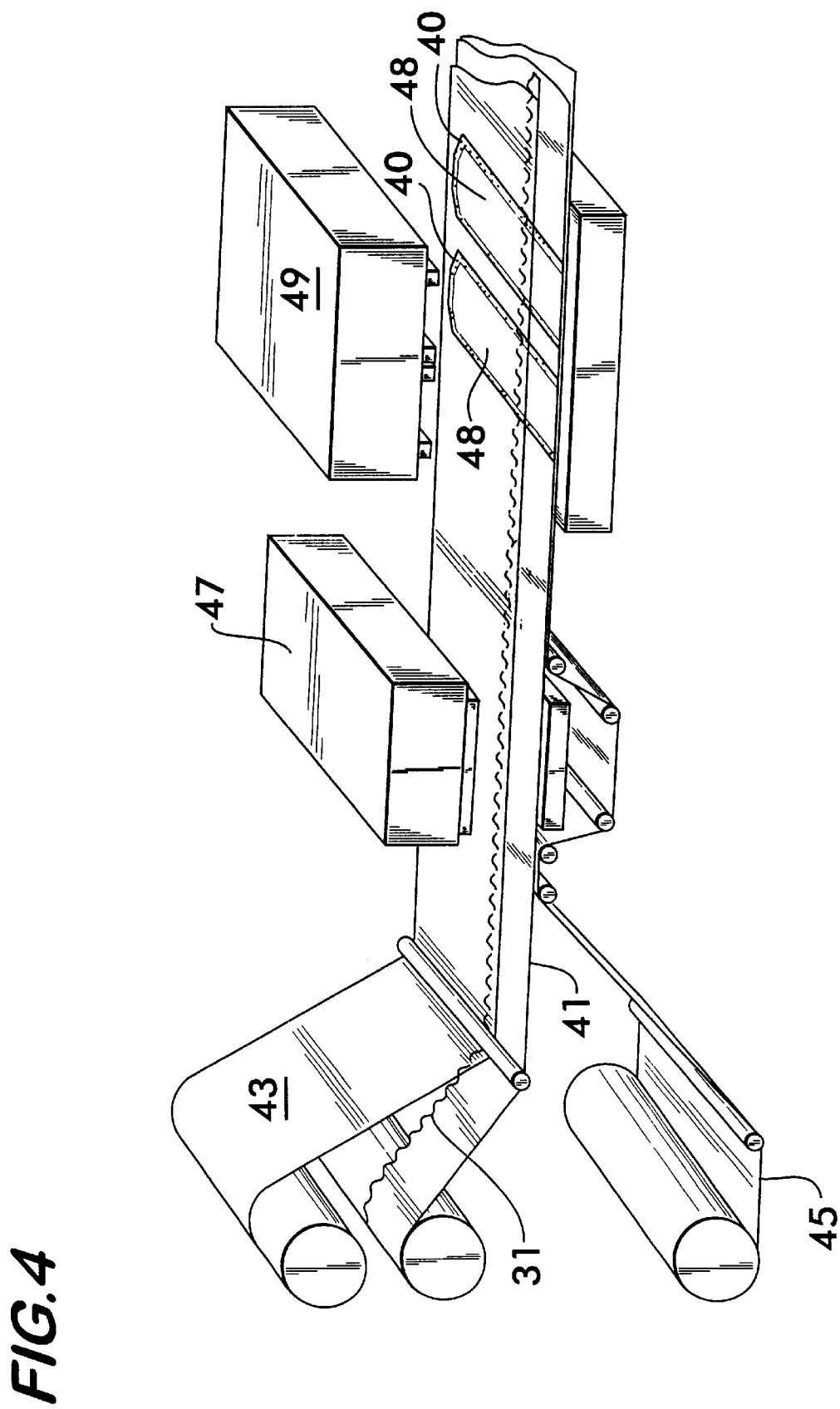
FIG. 4 is a top right front perspective view of the manufacturing process of the invention embodiment shown in FIGS. 5–6.

Referring now to FIG. 2, in a second sealing operation a second cross-seal 24 is applied by the packager to form a closure of the pouch mouth thus completely sealing the contents of the pouch after the packaged items are introduced. An area of seal overlap more clearly shown in FIG. 4 is created by this second heat-seal footprint 24, however with the present invention, enhanced web fusion in this area is provided by the unique wavy shape of the end portions of the interior boundary line 25 of the fused webs. This wavy shape provides a series of inward-facing peaks and valleys that creates greater boundary edge length which better receives the flow of web material when the second heat sealing die is forceably applied and thus the webs are more completely fused along this boundary. Furthermore, microbes are known to migrate in a straight line or channel, and therefore any possible gap in the materials along the line of the seal overlap must follow a tortuous path, thus preventing microbial propagation. Finally, the tortuous path that any contaminating microbes must follow is necessarily a longer path which further prevents contamination.

Referring now to FIG. 4, a diagram of the assembly process which forms pouches having a semipermeable panel is depicted. To address the problem with contamination along the lamination edge of spliced-on semipermeable panels described above, a tortuous boundary is also provided along the resulting transverse transition line between the spliced webs in a unique way. A tortuous path is formed having a wavy shape similar to the boundary line described in the embodiment of FIGS. 1–3, however in this embodiment, enhanced performance is obtained by cutting the wavy-shape into the edge of the intermediary material 31 in its raw state prior to assembly with the other webs of the pouch construction. In this instance, the semipermeable or "breather" panel is composed of a material such as Dupont Tyvek®. As shown in this diagram, the narrow strip of the semipermeable material 41 is spliced to a top web 43 thus forming one of the two pouch sidewalls. According to this process, the semipermeable strip 41 is first spliced to the top web 43 by primary pressure, dwell and heat-sealing 47 and then the bottom web is fused to the spliced pair of webs by a second heat-seal die 49 which applies a heat-seal footprint 40 that defines the outer edges of each pouch. In the diagram of FIG. 4, the heat seal die 49 is shown in which two pouches 48 are created side-by-side with the second heat-seal platen. Later, a shear cutter (not shown) severs the individual pouches from the host web material along their perimeters. Each pouch thus created will have a spliced-on panel of web material 41 at the top of each pouch and a three-ply area along the sides where all three webs are fused together as shown in FIGS. 5a and 6.

Figure 5:
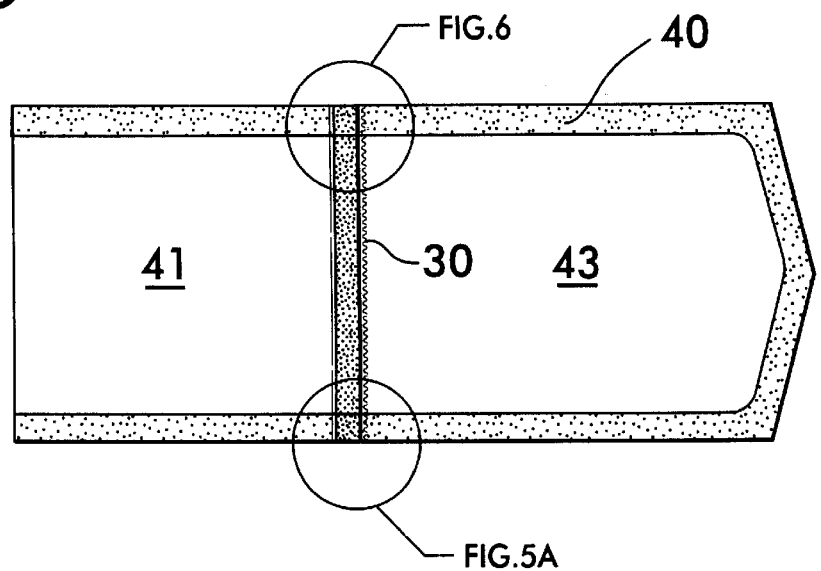
FIG. 5 top plan view of an alternate embodiment of the present invention.
Figure 5A:
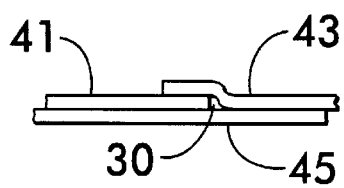
FIG. 5a is an enlarged fragmentary side view of the invention that is indicated in FIG. 5.
Figure 6:
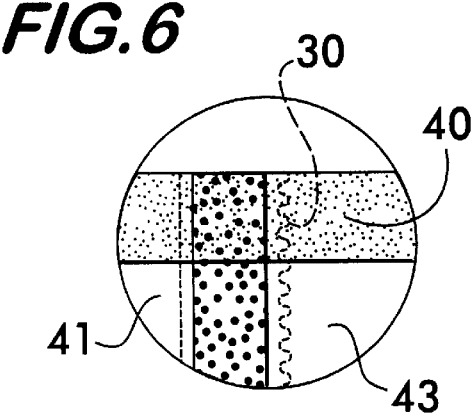
FIG. 6 is an enlarged fragmentary view of the view as indicated in FIG. 5.

By the manufacturing process depicted in FIG. 4, the resulting three-ply seal overlap construction shown in FIG. 5a is in the area where the primary splicing seal that attaches the Dupont Tyvek® material overlaps the secondary footprint seal (FIG. 6) and extends to the side edges of the panel. It will thus be readily understood that by this construction, there is a potential for a contamination channel 30 to be formed along the transverse boundary line where the two-ply top layer, (spliced webs 41 and 43) is fused to the bottom web 45 (creating a three-ply thickness). However, by this construction this channel is not a straight path, but wavy, due to the side edge configuration of the semipermeable web, thus creating a tortuous path for any migrating microbes. This provides the same advantages of preventing microbial contamination as the first embodiment shown in FIG. 1.

What is claimed is:

1. A pouch, comprising:

two webs positioned face-to-face having portions of their bottom and side edges joined by heat fusion thereby forming said pouch having an interior cavity;

a perimeter seal footprint being the area of fusion of said webs along said bottom and side edges;

a mouth of said pouch extending transversely along the entire length of a top edge of said webs;

an interior boundary line lying along the inside edge of said seal footprint facing said cavity, said boundary line having ends terminating at said mouth; and two end portions of said interior boundary line directly adjacent said mouth having a wavy configuration including a plurality of inward-facing peaks and valleys.

2. The pouch of claim 1 further including a transverse heat-seal closure, said closure having a footprint which extends across said top edge and overlaps said end portions of said boundary line.

3. The pouch of claim 1 wherein said peaks and valleys are further described as being radiused.

4. A pouch, comprising:

two opposing faces composed of heat-fusable sheet materials fused together in an area along their side and bottom edges;

one of the two opposing faces being two webs spliced together along a transverse seam which extends the entire width of said one face and overlaps a transverse edge of one of said webs, said transverse edge of said one of said webs having an inward-facing wavy configuration including a series of peaks and valleys fused between a second of said two opposing faces and a second of said two webs in said area where said opposing faces are fused together.

5. The pouch of claim 4 wherein said one of said webs is composed of a semipermeable material.

6. The pouch of claim 5 wherein said peaks and valleys are further described as being radiused.

* * * * *